(12) United States Patent
Türker et al.

(10) Patent No.: US 6,899,312 B2
(45) Date of Patent: May 31, 2005

(54) PRESSURE RELIEF VALVE FOR FLOWING MEDIA

(75) Inventors: Ahmet Türker, Lübeck (DE); Matthias Witt, Bad Schwartau (DE)

(73) Assignee: Dräger Medical AG & Co. KGaA, Lübeck (DE)

( * ) Notice: Subject to any disclaimer, the term of this patent is extended or adjusted under 35 U.S.C. 154(b) by 65 days.

(21) Appl. No.: 10/628,705

(22) Filed: Jul. 28, 2003

(65) Prior Publication Data

US 2004/0046136 A1 Mar. 11, 2004

(30) Foreign Application Priority Data

Sep. 5, 2002 (DE) .......................................... 102 40 992

(51) Int. Cl.[7] .............................................. F16K 17/06
(52) U.S. Cl. ...................... 251/83; 137/542; 137/543.13
(58) Field of Search ...................... 251/82, 83; 137/540, 137/542, 543, 543.13, 543.17

(56) References Cited

U.S. PATENT DOCUMENTS 4,932,434 A * 6/1990 Taylor ......................... 137/469

FOREIGN PATENT DOCUMENTS

DE 38 01 444 7/1989

* cited by examiner

Primary Examiner—Gregory L. Huson
Assistant Examiner—Peter deVore
(74) Attorney, Agent, or Firm—McGlew and Tuttle, P.C.

(57) ABSTRACT

A pressure relief valve for flowing media has a closing element (6), whose closing force can be set with both the setting of the closing force and the brief release of the closing element (6) performed with a single setting element. Teeth (22, 23) are provided, by which the threaded sleeve (3) can be actuated such that it can perform a rotary movement and a lifting movement can be performed between the handwheel (2) and the threaded sleeve (3). The teeth are provided between a pin (21) of the handwheel (2) for setting the closing force and a threaded sleeve (3). The closing element (6) is connected to the handwheel (2) such that the closing element (6) follows the lifting movement of the handwheel (2).

20 Claims, 5 Drawing Sheets

PRESSURE RELIEF VALVE FOR FLOWING MEDIA

FIELD OF THE INVENTION

The present invention pertains to a pressure relief valve with a closing element having a closing force that can be set and with a threaded sleeve that can be actuated by means of a handwheel for generating a variable closing force of the closing element as well as a valve shaft, which extends within the threaded sleeve toward the handwheel and is connected to the closing element.

BACKGROUND OF THE INVENTION

A pressure relief valve of this type has become known from DE 38 01 444 A1. The prior-art valve is used in the breathing gas line of an anesthesia apparatus or respirator to make possible the manual as well as the spontaneous respiration by the corresponding switching of a changeover switch. Thus, the valve is opened in the "manual respiration" mode by a possible overpressure in the breathing gas line against a preset closing force in order to release excess gas. The closing force is set by means of a handwheel and a valve spindle, and, depending on the position of the handwheel, a valve spring is compressed more or less strongly in order to thereby vary the opening pressure. In the "spontaneous respiration" mode, the closing element is released, by contrast, by the changeover switch, so that the closing force does not act any longer and the breathing gas can flow off without an appreciable expiration resistance. If the changeover switch is again shifted in the "manual respiration" direction, the original closing force again becomes established without corrections having to be made on the handwheel of the valve.

If complete pressure relief of the breathing gas line must be briefly performed during the manual respiration, this can be performed only if the changeover switch is shifted in the "spontaneous respiration" direction. However, it may now happen, especially when other settings also have to be performed on the anesthesia apparatus or respirator, that the operator forgets to shift the changeover switch to the "manual respiration" position. Delays may thus arise for the user in terms of the continuation of the manual respiration.

SUMMARY OF THE INVENTION

The basic object of the present invention is to improve a pressure relief valve of this type such that both the setting of the closing force and the brief release of the closing element can be performed with a single setting element without changing the set closing force in the process.

According to the invention, a pressure relief valve for flowing media is provided with a closing element having a closing force that can be set. A threaded sleeve is provided that can be actuated by a handwheel to generate a variable closing force of the closing element. A valve shaft extends within the threaded sleeve toward the handwheel and is connected to the closing element. The connecting element transmits the rotary movement of the handwheel to the threaded sleeve and makes possible a lifting movement. The connecting element is provided between the handwheel and the threaded sleeve. The connection of the valve shaft to the handwheel is designed such that the valve shaft follows the lifting movement of the handwheel.

The advantage of the present invention is essentially that the handwheel is connected to a threaded sleeve, which is used to set the closing force of the closing element, such that the rotary movement of the handwheel is transmitted to the threaded sleeve, on the one hand, and the handwheel can be actuated in relation to the threaded sleeve in such a way that it can perform a lifting movement, on the other hand. The handwheel is rigidly connected to the valve shaft accommodating the closing element, so that the closing element is also lifted off from the valve seat during the release of the handwheel.

The handwheel advantageously has a cylindrical pin, which is provided with external teeth and is directly connected to the valve shaft. The threaded sleeve, which is engaged by the pin, has, by contrast, internal teeth of a shape corresponding to the external teeth. Due to the meshing of the teeth, the rotary movement of the handwheel is transmitted to the threaded sleeve, on the one hand, while a relative movement is possible in the axial direction of the handwheel in relation to the threaded sleeve, on the other hand.

The threaded sleeve advantageously has three helically extending grooves located next to one another. The threaded sleeve is accommodated in a stationary cylinder, which has projections engaging the grooves. During its rotation, the threaded sleeve is displaced in the cylinder in the upward or downward direction. The threaded sleeve is in turn connected via a compression spring to the closing element, so that the closing force of the closing element is changed during the upward and downward movement of the threaded sleeve.

The grooves of the threaded sleeve advantageously have a different pitch in one section in order to make it possible to change the closing force of the closing element progressively. It may happen in the case of a linear adjustment of the closing force that a maximum closing force of, e.g., 70 mbar cannot be set with an acceptable scale in case of a preset angle of rotation of less than 360°. It should be taken into consideration in the case of such pressure relief valves that an accurate settability must be ensured in the range of up to about 40 mbar, whereas a coarse setting is sufficient at higher pressure values. Such a requirement can be met only if the closing force changes linearly up to about 40 mbar or 50 mbar and a progressive characteristic is selected at stronger closing forces. This characteristic can be set by selecting the pitch of the external thread on the threaded sleeve.

One exemplary embodiment of the present invention is shown in the figure and will be explained in greater detail below. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which the preferred embodiment of the invention is illustrated.

DESCRIPTION OF THE PREFERRED EMBODIMENT

Figure 1:
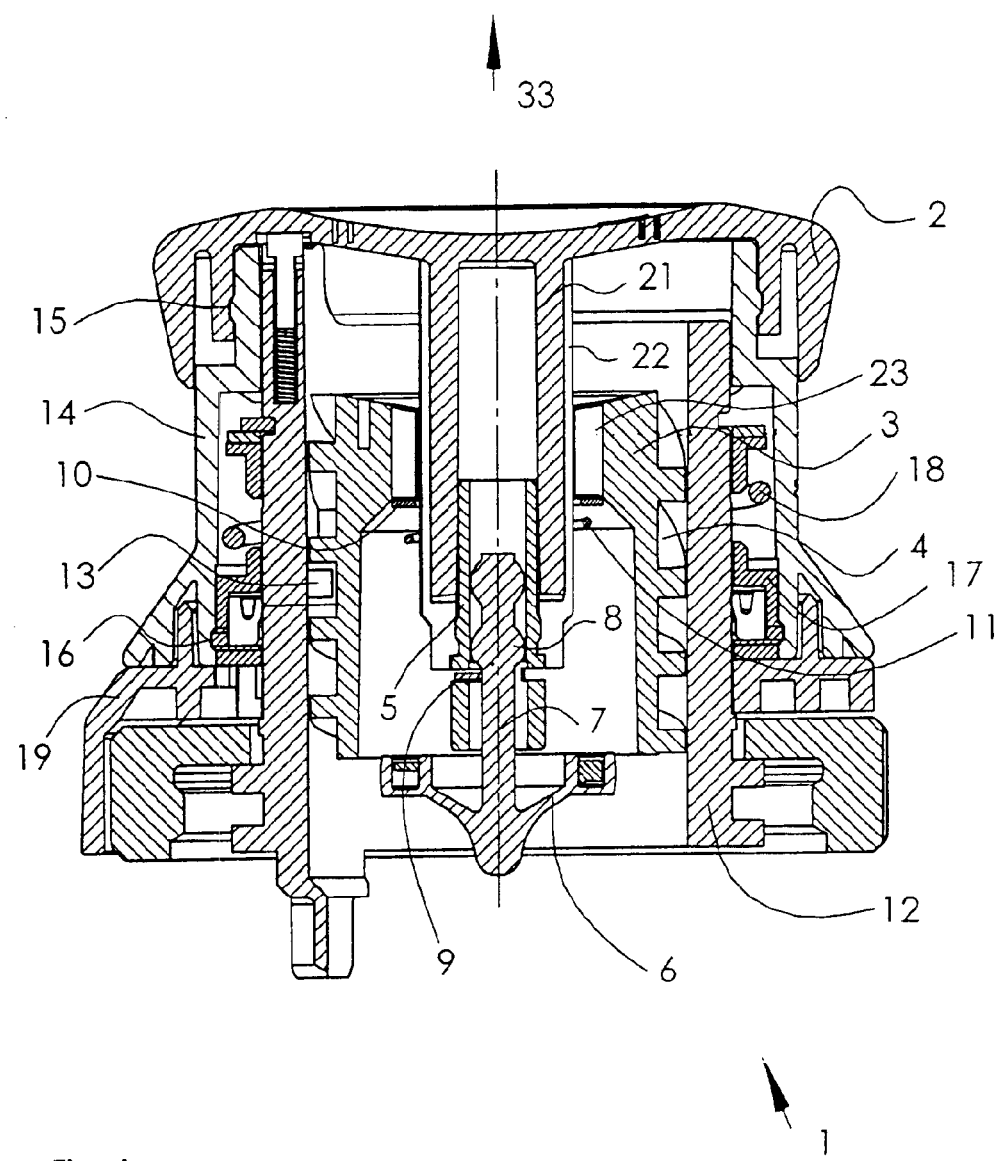
FIG. 1 is a longitudinal sectional view of a pressure relief valve according to the present invention.

Referring to the drawings in particular, FIG. 1 shows the longitudinal section of a pressure relief valve 1 with a handwheel 2, a threaded sleeve 3, which is connected to the handwheel 2 in such a way that it can perform a lifting movement and a rotary movement, and grooves 4 located on the outside, as well as a valve shaft 5 rigidly connected to the handwheel for a valve disk 6 as a closing element guided therein in such a way that it can perform a lifting movement. The valve disk 6 has a guide bar 7 protruding into the valve shaft 5 with a bead 8, wherein the bead 8 is fixed in the valve shaft 5 by means of a retaining ring 9. A compression spring 11 is located between the valve disk 6 and a contact surface 10 at the threaded sleeve 3, but only the turn of the compression spring 11 in the area of the contact surface 10 is shown for the sake of greater clarity. The threaded sleeve 3 is accommodated in a cylinder 12, which has projections 13 distributed over the circumference on its inner side, the projections 13 engaging the grooves 4. Only one of the projections 13 is shown in FIG. 1 for the sake of greater clarity.

The pressure relief valve 1 has on its outer side a protective sleeve 14, which is in turn connected to the handwheel 2 via a first snap-in connection 15 and to a support ring 17 via a second snap-in connection 16, wherein the support ring 17 is axially displaceable on the outer side of the cylinder 12 and is supported against the cylinder 12 via a spring 18. The threaded sleeve 14 is in contact on the underside with a guide ring 19, which is fastened to the cylinder 2 via locking cams 20 (FIG. 2).

Figure 2:
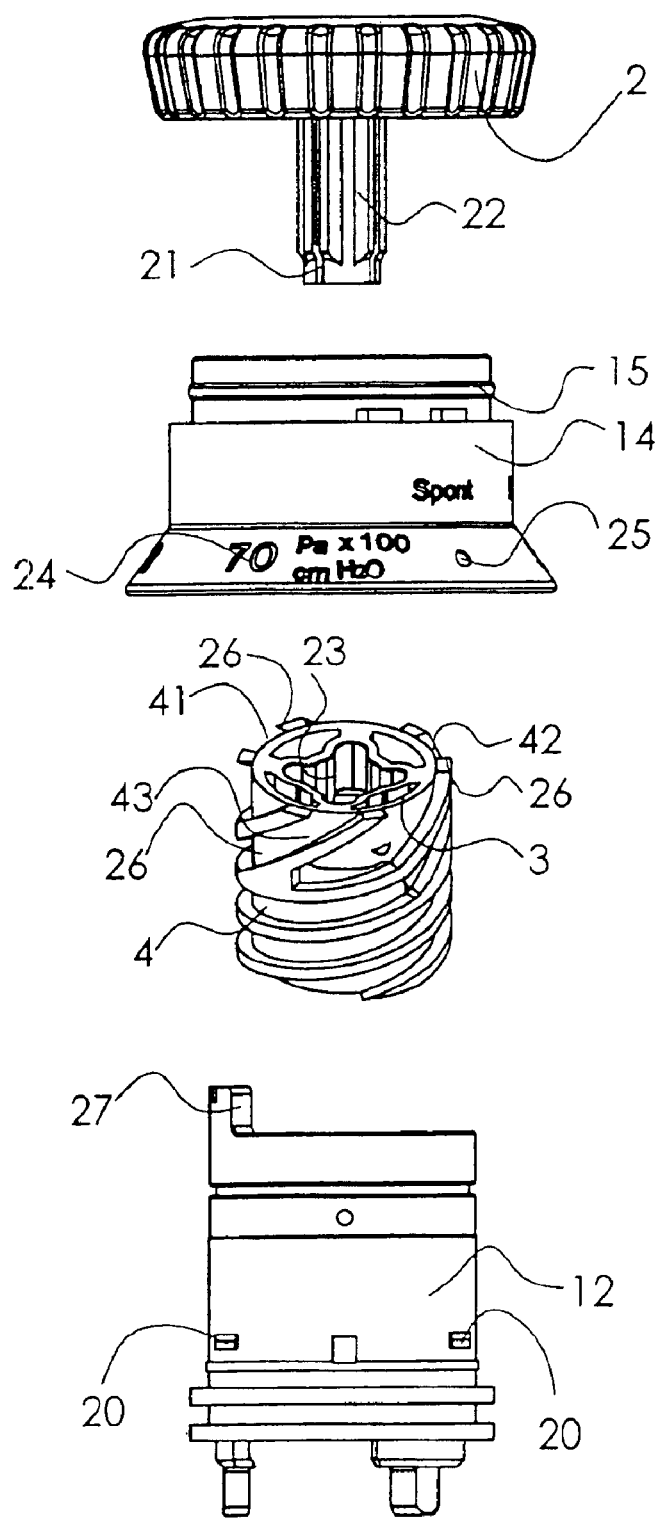
FIG. 2 is an exploded view of some components of the pressure relief valve according to FIG. 1.

FIG. 2 illustrates in an exploded view the handwheel 2, the protective sleeve 14 with the first snap-in connection 15, the threaded sleeve 3 and the cylinder 12. Identical components are designated with the same reference numbers as in FIG. 1. The threaded sleeve 3 is illustrated in the perspective view for the sake of greater clarity.

The handwheel 2 has on its underside a pin 21 with external teeth 22, which pin engages the threaded sleeve 3 with internal teeth 23 having a shape corresponding thereto. A rotary movement of the handwheel 2 is transmitted by means of the teeth 22, 23 to the threaded sleeve, and an axial displacement of the handwheel 2 in relation to the threaded sleeve 3 is also possible. The protective sleeve 14 has a scale 24 on its outside for various pressure values as well as an end position 25 for spontaneous respiration.

The grooves 4 on the threaded sleeve 3 comprise three individual grooves 41, 42, 43, which are arranged offset by 120°, extend helically on the outside of the threaded sleeve 3 and have end sections 26 with an increased pitch. On its top side pointing toward the handwheel 2, the cylinder 12 has a carrier 27, which is located beneath the handwheel 2.

Figure 3:
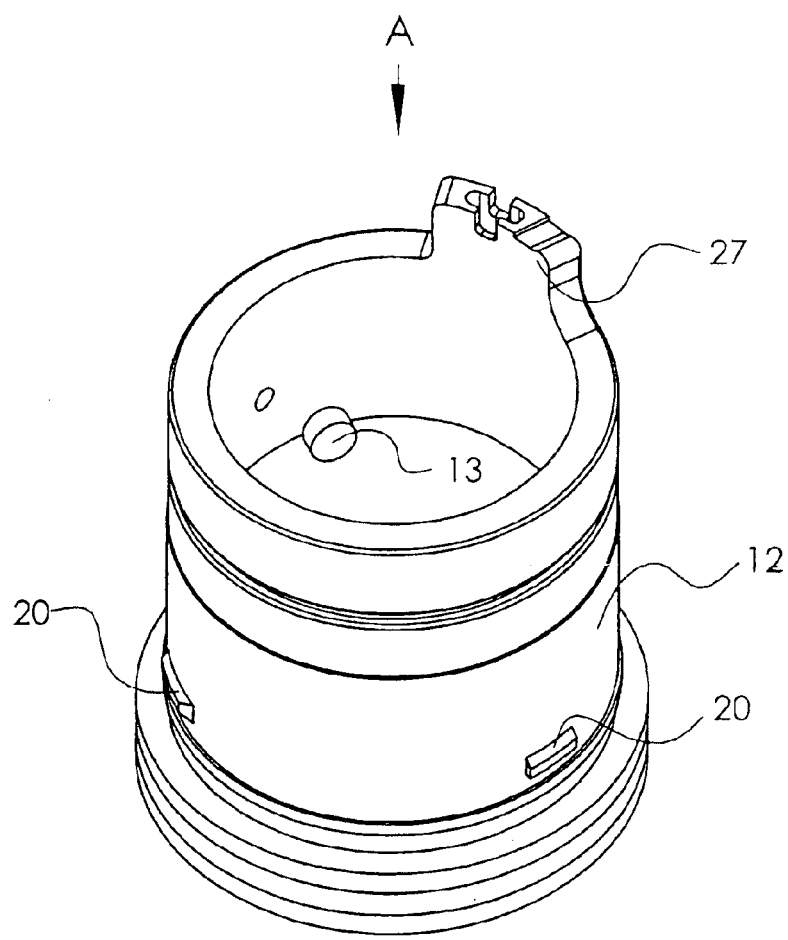
FIG. 3 is a perspective view of the cylinder.

FIG. 3 shows a perspective view of the cylinder 12 with the projections 13 located on the inside, the carrier 27 and the locking cams 20 for the guide ring 19 corresponding to FIG. 1.

Figure 4:
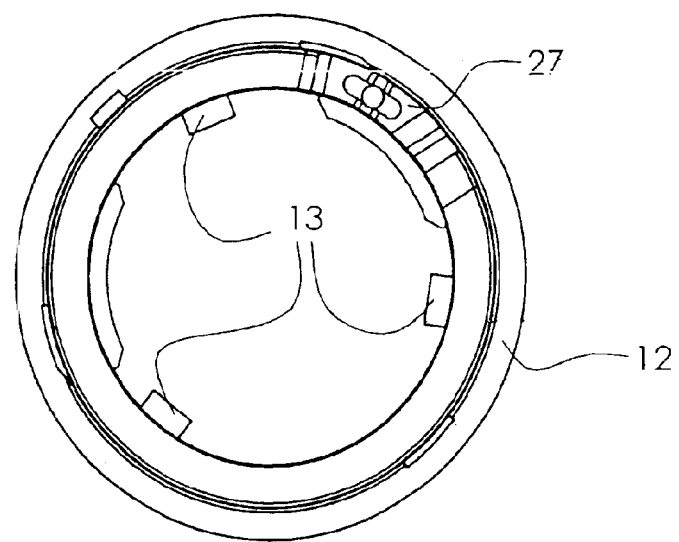
FIG. 4 is a top view of the cylinder in direction of view A according to FIG. 3.

FIG. 4 shows a top view of the cylinder 12 in direction of view A according to FIG. 3 with three projections 13, which are offset by 120° in relation to one another and engage the grooves 41, 42, 43 of the threaded sleeve 3, FIG. 2. The cooperation between the grooves 41, 42, 43 and the projections 13 causes the threaded sleeve 3 to be axially displaced within the cylinder 12 upward or downward during its rotation.

Figure 5:
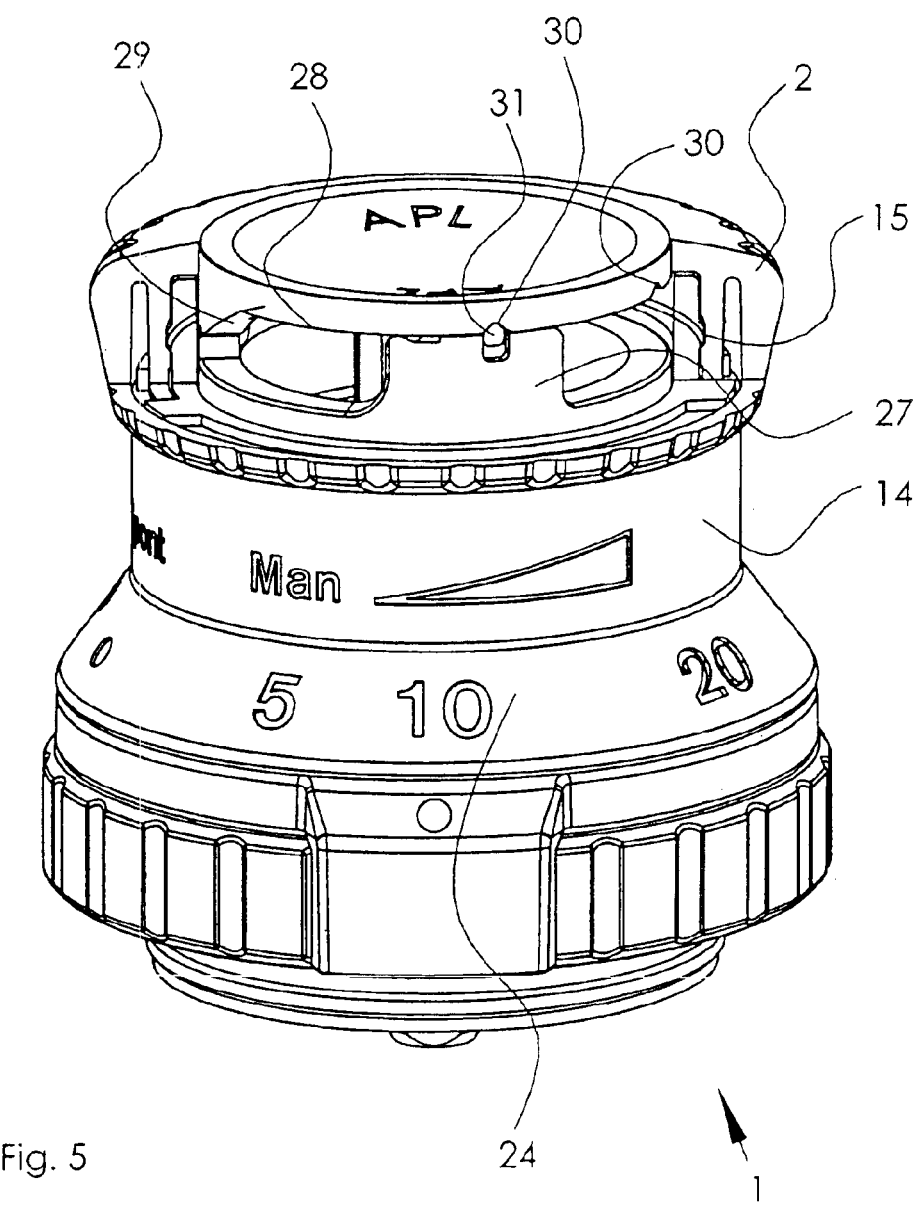
FIG. 5 is a side view of the pressure relief valve with the partially cut-away handwheel.

FIG. 5 shows a side view of the pressure relief valve 1 with a partially cut-away handwheel 2. The carrier 27 of the cylinder 12 extends here on an annular sliding surface 28, which ends in an oblique plane 29. The sliding surface 28 has notches 30, which correspond to settings of the scale 24 and send a tactile feedback for settings, which equal an integer multiple of 10 mbar, via an elastic locking member 31, which is located at the carrier 27.

The scale 24 comprises a range of 5 mbar to 70 mbar, wherein the setting takes place in equidistant sections between integer multiples of 10 mbar up to about 50 mbar, whereas the end sections 26 of the grooves 41, 42, 43, FIG. 2, are used with a progressive adjustment of the compression spring 11 (FIG. 1) between 50 mbar and 70 mbar. The progressive adjustment of the closing force in the area between 50 mbar and 70 mbar is necessary to still be able to set the maximum of 70 mbar with sufficient accuracy at a maximum angle of rotation of less than 360°. A compromise must be found here between the most accurate possible setting of the opening pressure up to about 50 mbar with a sufficiently large setting angle and a maximum opening pressure of 70 mbar, which can be set with greater tolerance, within a maximum adjustment angle of less than 360° for the handwheel.

Figure 6:
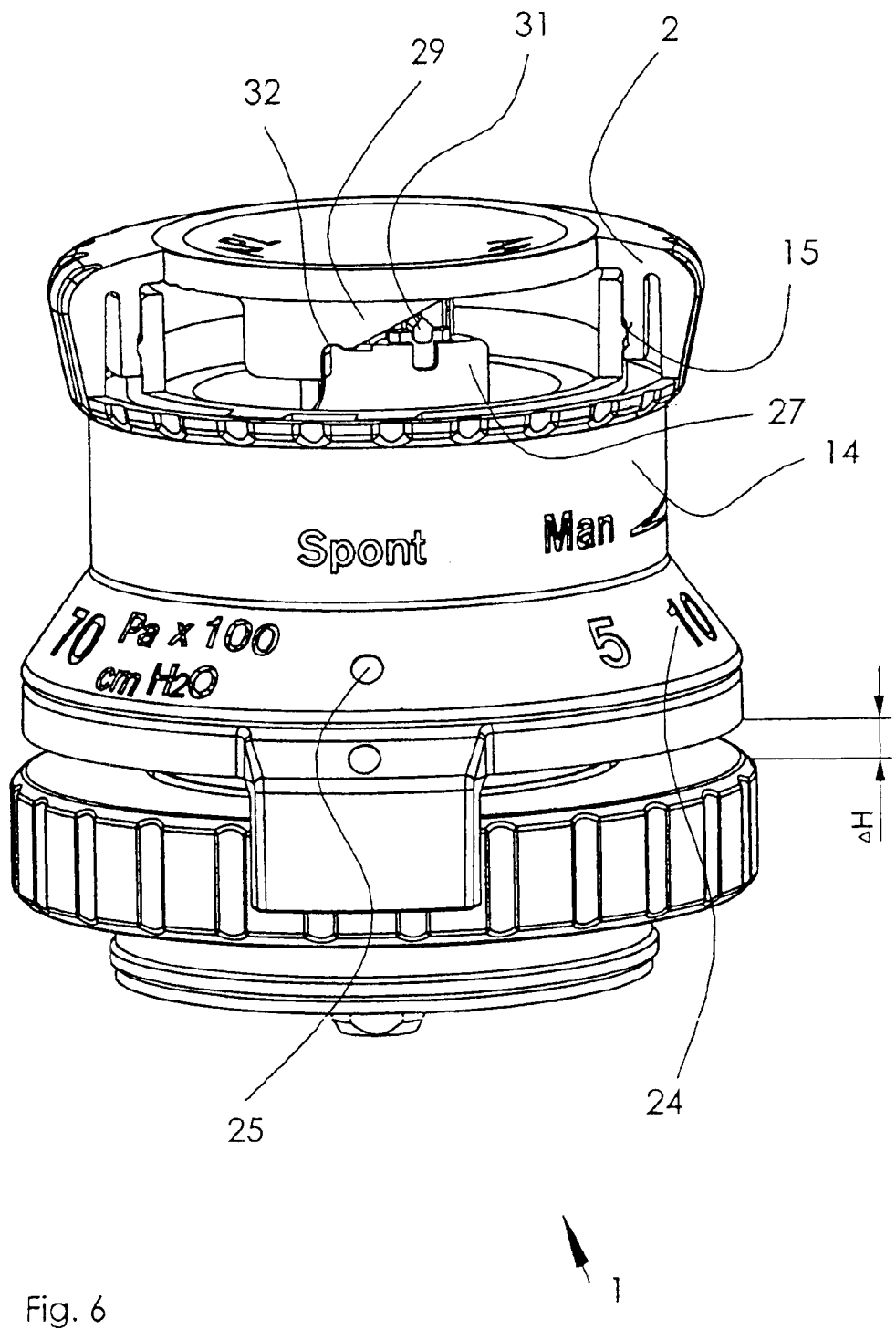

FIG. 6 illustrates a side view of the pressure relief valve 1, in which the handwheel 2 is cut up in the area of the oblique plane 29 compared with FIG. 5. The oblique plane 29 becomes active when the handwheel 2 is rotated below a setting of 5 mbar of the scale 24 in the direction of the end position 25 for spontaneous respiration. The handwheel 2 is now raised by ΔH together with the protective sleeve 14 by the carrier 27 and the locking member 31, and the locking member 31 snaps into the recess 32 in the end position 25 and blocks the handwheel 2 in the end position 25.

The pressure relief valve 1 according to the present invention operates as follows:

Depending on the rotary movement of the handwheel 2 (FIG. 1) the threaded sleeve 3 is moved upward or downward, and the pretension of the compression spring 11 which is in contact with the valve disk 6 changes in the process. The valve disk 6 now lies on a valve seat of a breathing gas line, where the valve seat is not shown specifically and the breathing gas line is not shown. Depending on the pretension of the compression spring 11, different pressure values will be obtained corresponding to the scale 24, at which pressure values the valve disk 6 is lifted off from the valve seat, i.e., at which the pressure relief valve 1 opens and excess breathing gas can escape. Regardless of the angular position of the handwheel 2 within the scale 24, the pressure relief valve 1 can be opened at any time without the setting performed previously having to be changed. The handwheel 2 is pulled for this purpose upward along the arrow 33, while the valve shaft 5 firmly connected to the handwheel 2, and the guide bar 7 with the valve disk 6, follow the movement of the of the handwheel 2. As can be determined from FIG. 2, the pin 21 with the external teeth 22 slides within the internal teeth 23 of the threaded sleeve 3 during the pulling movement of the handwheel 2. The spring 18 (FIG. 1) is compressed during the pulling movement of the handwheel 2, and it exerts a restoring force on the handwheel 2 via the support ring 17 and the protective sleeve 14.

As can be determined from FIG. 6, the open position of the pressure relief valve 1 is also reached when the handwheel 2 is rotated from the scale 24 in the direction of the end position 25. The locking member 31 now slides along the oblique plane 29 up to the recess 32, as a result of which the handwheel is raised by ΔH together with the protective sleeve 14.

While a specific embodiment of the invention has been shown and described in detail to illustrate the application of the principles of the invention, it will be understood that the invention may be embodied otherwise without departing from such principles.

What is claimed is:

1. A pressure relief valve for flowing media, the pressure relief valve comprising:
    a closing element having a settable closing force;
    a handwheel;
    a threaded sleeve rotated by said handwheel to move axially for generating a variable closing force of the closing element;
    a valve shaft extending within said threaded sleeve toward the handwheel and being connected to the closing element;
    a connecting element transmitting the rotary movement of said handwheel to said threaded sleeve while not transmitting axial movement of said handwheel to said threaded sleeve for providing a lifting movement between said handwheel and said threaded sleeve, said valve shaft being connected to said handwheel such that said valve shaft follows said lifting movement of said handwheel.

2. A pressure relief valve in accordance with claim 1, wherein said connecting element comprises teeth.

3. A pressure relief valve in accordance with claim 1, wherein said handwheel has a cylindrical pin provided with external teeth, said cylindrical pin being connected to said valve shaft, and said threaded sleeve has internal teeth corresponding to said external teeth, said external teeth and said internal teeth comprising said connecting element.

4. A pressure relief valve in accordance with claim 2, wherein said connecting element comprises external teeth provided on a cylindrical pin of said handwheel, and internal teeth on said threaded sleeve.

5. A pressure relief valve in accordance with claim 1, wherein said threaded sleeve has externally located helically extending grooves.

6. A pressure relief valve in accordance with claim 5, wherein said threaded sleeve is accommodated in a cylinder having projections on an inner side, said projections engaging grooves formed by threading of said threaded sleeve.

7. A pressure relief valve in accordance with claim 5, wherein said grooves have at least one section with a different pitch from other sections or a remaining section, said section with a different pitch progressively changing the closing force.

8. A pressure relief valve in accordance with claim 6, wherein said grooves have at least one section with a different pitch from other sections or a remaining section, said section with a different pitch progressively changing the closing force.

9. A pressure relief valve comprising:
    a valve closing element;
    a valve shaft connected to said closing element;
    a handwheel;
    a sleeve connected to said handwheel for generating a variable closing force exerted on said valve closing element, said valve shaft extending within said sleeve toward said handwheel;
    a connecting element transmitting a rotary movement of said handwheel to said sleeve for rotation of said sleeve upon rotation of said handwheel while not transmitting axial movement of said handwheel to said sleeve for allowing said handwheel to move axially relative to said sleeve providing a lifting movement between said handwheel and said sleeve, said valve shaft being connected to said handwheel such that said valve shaft follows the lifting movement of said handwheel.

10. A pressure relief valve in accordance with claim 9, wherein said connecting element comprises teeth.

11. A pressure relief valve in accordance with claim 9, wherein said handwheel has a cylindrical pin provided with external teeth, said cylindrical pin being connected to said valve shaft, and said threaded sleeve has internal teeth corresponding to said external teeth, said external teeth and said internal teeth comprising said connecting element.

12. A pressure relief valve in accordance with claim 10, wherein said connecting element comprises external teeth provided on a cylindrical pin of said handwheel, and internal teeth on said threaded sleeve.

13. A pressure relief valve in accordance with claim 9, wherein said sleeve has externally located helically extending grooves.

14. A pressure relief valve in accordance with claim 13, wherein said sleeve is accommodated in a cylinder having projections on an inner side, said projections engaging said grooves formed by threading of said sleeve.

15. A pressure relief valve in accordance with claim 13, wherein said grooves have at least one section with a different pitch from other sections or a remaining section, said section with a different pitch progressively changing the closing force.

16. A pressure relief valve in accordance with claim 14, wherein said grooves have at least one section with a different pitch from other sections or a remaining section, said section with a different pitch progressively changing the closing force.

17. A pressure relief valve comprising:
    a support cylinder with a projection;
    a valve closing element;
    a valve shaft connected to said closing element;
    a handwheel mounted for rotation relative to said support cylinder and for axial movement relative to said support cylinder;
    a sleeve with a treaded region engaging said projection for axial movement of said sleeve upon rotational movement of said sleeve;
    a connecting means for transmitting a rotary movement of said handwheel to said sleeve for rotation of said sleeve upon rotation of said handwheel while allowing said handwheel to move axially relative to said sleeve for allowing a lifting movement between said handwheel and said sleeve, said valve shaft being connected to said handwheel such that said valve shaft follows the axial lifting movement of said handwheel.

18. A pressure relief valve in accordance with claim 17, wherein
    said connecting means comprises a cylindrical pin provided with external axially extending teeth, said cylindrical pin being connected to said valve shaft, and said threaded sleeve having internal teeth corresponding to said external teeth, said external teeth and said internal teeth comprising said connecting element.

19. A pressure relief valve in accordance with claim 17, wherein said sleeve treaded region is located on an outer surface of said sleeve and comprises helically extending grooves.

20. A pressure relief valve in accordance with claim 19, wherein said grooves have at least one section with a different pitch from other sections or a remaining section, said section with a different pitch progressively changing the closing force.

* * * * *